(12) United States Patent
McCloy et al.

(10) Patent No.: US 7,945,311 B2
(45) Date of Patent: May 17, 2011

(54) RETROREFLECTIVE MARKER-TRACKING SYSTEMS

(75) Inventors: Bradley J. McCloy, New Hamburg (CA); Georg Brunner, Constance (DE)

(73) Assignee: Northern Digital Inc., Waterloo, Ontario (CA)

( * ) Notice: Subject to any disclaimer, the term of this patent is extended or adjusted under 35 U.S.C. 154(b) by 996 days.

(21) Appl. No.: 11/673,131

(22) Filed: Feb. 9, 2007

(65) Prior Publication Data
US 2007/0183041 A1    Aug. 9, 2007

Related U.S. Application Data

(60) Provisional application No. 60/772,331, filed on Feb. 9, 2006.

(51) Int. Cl.
*A61B 5/05* (2006.01)

(52) U.S. Cl. ..... 600/424; 600/414; 600/426; 356/152.3; 398/169; 398/170; 427/163.1; 427/163.4

(58) Field of Classification Search .................. 600/414, 600/424, 426; 398/169, 170; 356/152.3; 427/163.1, 163.4
See application file for complete search history.

(56) References Cited

U.S. PATENT DOCUMENTS

| | | | |
|---|---|---|---|
| 4,983,463 A | | 1/1991 | Minford et al. |
| 5,670,209 A | * | 9/1997 | Wyckoff ...................... 427/215 |
| 6,285,959 B1 | | 9/2001 | Greer |
| 7,137,712 B2 | | 11/2006 | Brunner et al. |
| 2003/0016368 A1 | | 1/2003 | Aman et al. |
| 2006/0073307 A1 | * | 4/2006 | Rossner et al. ............... 428/143 |

OTHER PUBLICATIONS

'Reflector Technology' [online] [retrieved Feb. 9, 2007] <URL: http://www.swareflex.com/5ueber-swareflex/t-rueckstrahler.html> 11 pages.
'Opti-Curb: Optical 360 Degree reflective curb markers' [online] [retrieved Feb. 9, 2007] URL:http://www.usreflector.com/html 6 pages.
'ARMORSTUD: Optical 360 Degree reflective pavement markers' [online] [retrieved Feb. 9, 2007] <URL: http://www.usreflector.com/Html> 9 pages.

* cited by examiner

*Primary Examiner* — Brian Casler
*Assistant Examiner* — James Kish
(74) *Attorney, Agent, or Firm* — Fish & Richardson P.C.

(57) ABSTRACT

A marker-tracking system includes an object, a marker illuminating device, a marker sensing device, and a computing device. The object includes a first retroreflective marker having a shape that is substantially defined by two spherical caps of different radii that are disposed substantially concentric in relation to one another. The marker illuminating device substantially illuminates the first retroreflective marker, the marker sensing device detects the illuminated first retroreflective marker and generates first data indicative of the location of the illuminated first retroreflective marker in space, and the computing device processes the first data generated by the marker sensing device to determine a position and/or orientation of the object in space.

43 Claims, 9 Drawing Sheets

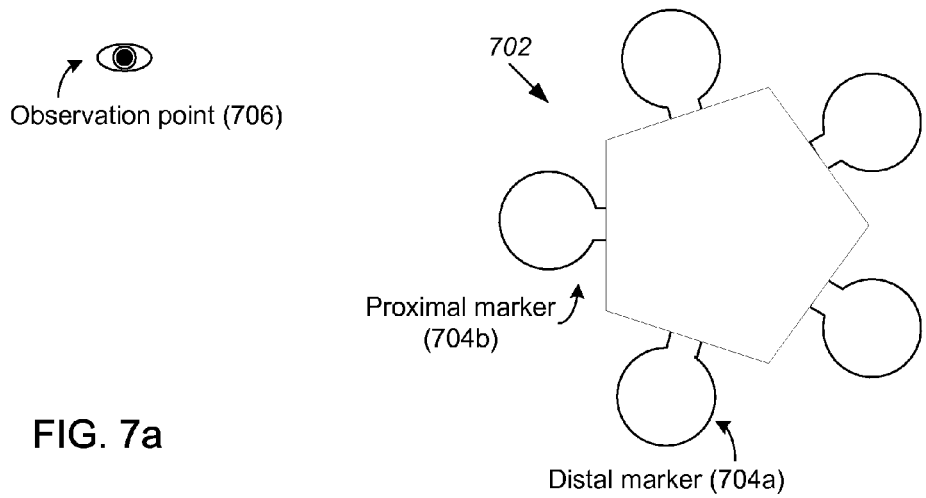
FIG. 7a
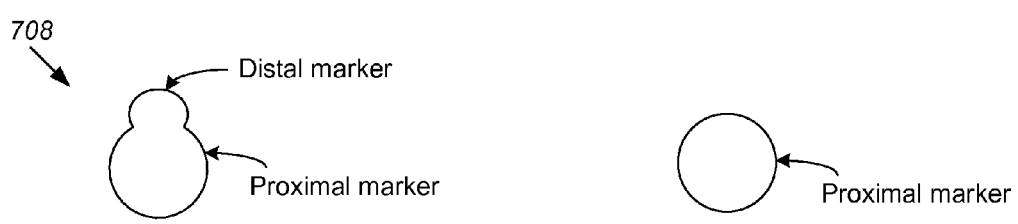
FIG. 7b
FIG. 7d
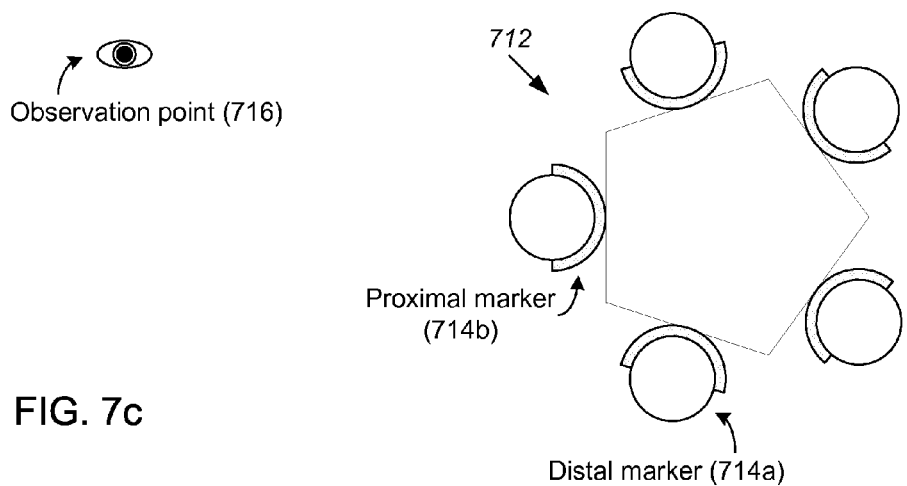
FIG. 7c

Actual obstruction (side view)

Image of marker with partial occlusion due to virtual obstruction

Image of marker with partial occlusion due to actual obstruction (front view of enhanced retroreflective marker)

RETROREFLECTIVE MARKER-TRACKING SYSTEMS

CROSS-REFERENCE TO RELATED APPLICATIONS

This application claims priority under 35 U.S.C. §119(e) to U.S. Patent Application Ser. No. 60/772,331, filed on Feb. 9, 2006, the entire contents of which are hereby incorporated by reference.

BACKGROUND

This description relates to retroreflective marker-tracking systems.

Known systems for obtaining coordinates of a point or points of interest include marker-tracking systems. Such marker-tracking systems typically rely on objects having one or more markers affixed thereto. The markers that are affixed to the object may be active markers (e.g., light emitting diode markers), passive markers (e.g., retroreflective markers), or a combination of active and passive markers.

In a medical application context, a user (e.g., a doctor) touches the surface of interest (e.g., a surface of a patient's body) using a distal tip of an object (e.g., a probe or a surgical instrument). A marker sensing device (e.g., a pair of cameras) views the marker(s) affixed to the object. On the basis of the known locations of the cameras and the location of the marker(s) as seen by each camera, such systems calculate the three-dimensional coordinates of the marker(s). Then, on the basis of the known relationship between the location of the marker(s) and the location of the object tip, the marker-tracking system determines the coordinates of the object's tip. With the object's tip on the surface, those coordinates also correspond to the coordinates of the surface at that point.

One example of a passive marker is based on glass bead technology. Such a passive marker (referred to in this description as a "multi-lens high refractive index marker") is formed by embedding tiny glass beads 902 (e.g., numbered in the hundreds or thousands) in a substrate 904 (a close up of which is shown in FIG. 9), and coating a surface (e.g., a sphere) with the substrate. The highly-textured surface of the sphere is susceptible to contamination from dirt, finger oils, etc. Any contamination that is present on the surface of the sphere may affect the retroreflective performance of the passive marker, thereby contributing or causing inaccuracies in the determination of a position of the object to which the marker is affixed.

True retroreflection connotes a manner of reflection where energy is directed back toward its source. At times, in practice, the observation point (e.g. the marker sensing device) cannot be located in a manner so as to allow observation of true retroreflected energy.

SUMMARY

In general, in one aspect, a system includes an object including a first retroreflective marker having a shape that is substantially defined by two spherical caps of different radii that are disposed substantially concentric in relation to one another, a marker illuminating device for substantially illuminating the first retroreflective marker, a marker sensing device for detecting the illuminated first retroreflective marker and for generating first data indicative of the location of the illuminated first retroreflective marker in space, and a computing device for processing the first data generated by the marker sensing device to determine a position and/or orientation of the object in space.

Implementations of the system include one or more of the following.

The shape of the first retroreflective marker may be further defined by one or more flanges.

The first retroreflective marker may have a uniform refractive index.

The first retroreflective marker may retroreflect light when light rays emanating from the marker illuminating device enter the first retroreflective marker within entrance angles ranging between $0°$ and $\pm\beta°$.

The shape that defines the first retroreflective marker may be formed by a sphere and a spherical cavity that are separated by a medium. The sphere may be defined by a radius R1; and the spherical cavity may be defined by an inner radius R2, an outer radius R3, a height h, and a base radius a. The outer radius R3 of the spherical cavity may be substantially equal to the height h of the spherical cavity, greater than the height h of the spherical cavity, or less than the height h of the spherical cavity. The inner radius R2 of the spherical cavity may be substantially equal to the radius R1 of the sphere, or greater than the radius R1 of the sphere. A reflective material may be applied directly on a cavity-side surface of the spherical cavity, a non-cavity-side surface of the spherical cavity, and/or a surface of the sphere.

The shape that defines the first retroreflective marker may be formed by a first spherical cap and a second spherical cap. The first spherical cap may be defined by a radius R4, a height h1, and a base radius a1; and the second spherical cap may be defined by a radius R5, a height h2, and a base radius a2. The height h1 may be greater than the radius R4. The height h2 may be greater than the radius R5. The height h1 may be substantially equal to the radius R4 and the height h2 may be substantially equal to the radius R5. A reflective material may be applied directly on a surface of the first or the second spherical cap.

The shape that defines the first retroreflective marker is formed by a first spherical cap component and a second spherical cap component, the first and the second spherical cap components being constructed as an integral unit. The first spherical cap component may be defined by a radius R6, a height h3, and a base radius a3; and the second spherical cap component may be defined by a radius R7, a height h4, and a base radius a4. The height h3 may be greater than the radius R6. The height h4 may be greater than the radius R7. The height h3 may be substantially equal to the radius R6 and the height h4 may be substantially equal to the radius R7. A reflective material may be applied directly on a surface of the first or the second spherical cap component.

The first retroreflective marker may be formed of a shatter-resistant material. The first retroreflective marker may be formed of a material having a relatively low refractive index. The first retroreflective marker may be formed of a material having a relatively high refractive index.

A reflective material may be applied directly on a rear surface of the first retroreflective marker.

A reflective material may be applied directly on one or more portions of a rear surface of the first retroreflective marker. The one or more portions of the rear surface of the retroreflective marker upon which the reflective material is applied may include less than an entirety of the rear surface.

The first retroreflective marker may be configured to diffusely retroreflect light.

The object of the system may further include at least one other retroreflective marker having a shape that is substantially defined by two spherical caps of different radii that are disposed substantially concentric in relation to one another. The first retroreflective marker and the at least one other retroreflective marker may be disposed on the object relative to one another such that only one of the retroreflective markers retroreflects light at a time when the retroreflective markers are simultaneously illuminated by the marker illuminating device. The first retroreflective marker and the at least one other retroreflective marker may be disposed on the object relative to one another such that at least two retroreflective markers retroreflect light when the retroreflective markers are simultaneously illuminated by the marker illuminating device. The marker sensing device of the system may detect the at least one other illuminated retroreflective marker, and for each detected marker, generate data indicative of the location of the respective illuminated marker in space. The computing device of the system may process the data generated by the marker sensing device to determine the position and/or orientation of the object in space. The retroreflective markers may be sized and dimensioned such that the marker sensing device detects a single discrete source of reflected light when the marker illuminating device illuminates the retroreflective markers simultaneously. The retroreflective markers may be sized and dimensioned such that the marker sensing device detects multiple discrete sources of reflected light when the marker illuminating device illuminates the retroreflective markers simultaneously. At least one of the multiple discrete sources of reflected light may be formed when the marker illuminating device illuminates at least two retroreflective markers simultaneously.

The radii of the spherical caps that substantially define the shape of the first retroreflective marker may be selected so that an intensity of a reflected light image that is detected when the first retroreflective marker is illuminated remains relatively constant even as an observation angle between the marker illuminating device and the marker sensing device varies.

DESCRIPTION OF DRAWINGS

FIG. 7a shows a device with respect to an observation point of a marker-tracking system, the device including five multi-lens high refractive index markers.

FIG. 7b shows a view of a proximal marker and a distal marker from the observation point of FIG. 7a.

FIG. 7c shows a device with respect to an observation point of a marker-tracking system, the device including five enhanced retroreflective markers.

FIG. 7d shows a view of a proximal marker from the observation point of FIG. 7c.

DETAILED DESCRIPTION

Figure 1:
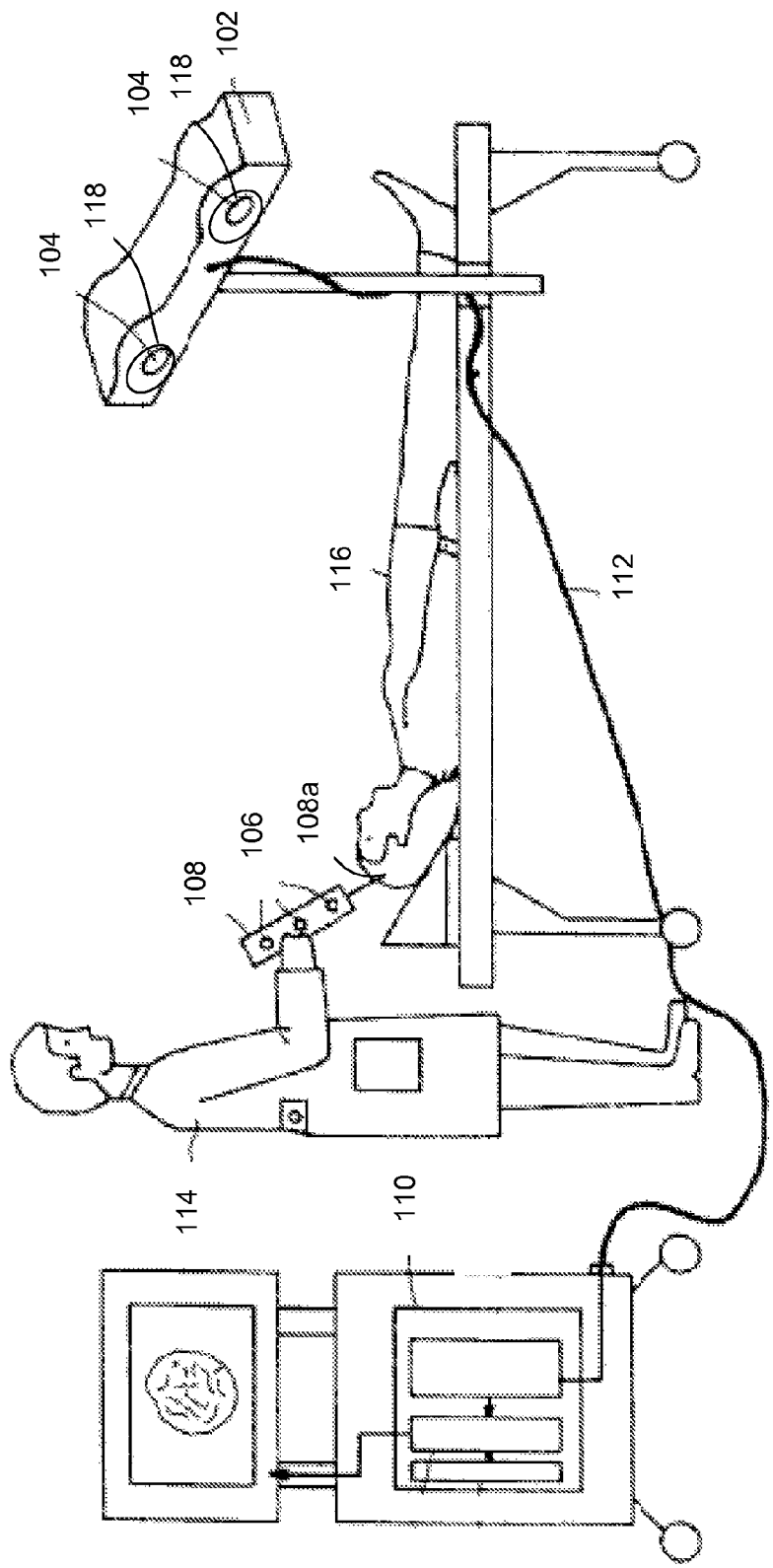
FIG. 1 shows a marker-tracking system in a medical application context.

Referring to FIG. 1, a marker-tracking system includes a unit 102 in which a marker sensing device (e.g., cameras 104) and a marker illuminating device 118 are rigidly mounted. The marker illuminating device 118 illuminates passive markers 106 that are affixed to an object, such as a tool 108. The cameras 104 detect the illuminated passive markers 106, generate data indicative of the location of the detected retroreflective markers 106 in space, and provide the data to a computing device. In the depicted example, the computing device is located within a computer 110 that is connected to the cameras 104 via wired communication links 112. In other examples, the computing device is located within the camera mounting unit 102 or located in a computer that is in communication with the cameras 104 via wireless communication links. Given the known locations of the cameras 104 and the locations of the passive markers 106, the computing device calculates a position and/or orientation of the tool 108. Further, on the basis of the known relationship between the location of each of the passive markers 106 and the location of a tip 108a of the tool 108, the computing device calculates the coordinates of the tool tip 108a in space. In those instances in which the tool 108 is handled by a user (e.g., a surgeon 114) and the tool tip 108a is pressed against or is otherwise in contact with a surface (e.g., a body 116 of a patient), the coordinates of the tool tip 108a correspond to the coordinates of the point at which the tool tip 108a contacts the surface.

In this description, various examples and implementations of passive markers (referred to in this description as "enhanced retroreflective markers") that may be included in the marker-tracking system of FIG. 1 are described. Common to all of the examples and implementations is the following: each enhanced retroreflective marker 106 of the system of FIG. 1 has a shape that is generally defined by two spherical caps: spherical cap A defined by a region of a sphere of radius $R_A$ that lies above (or below) a plane $P_A$, spherical cap B defined by a region of a sphere of radius $R_B$ that lies above (or below) a plane $P_B$, where $R_A \neq R_B$. In all implementations, the two spherical caps are disposed substantially concentric in relation to one another (i.e., the sphere of radius $R_A$ and the sphere of radius $R_B$ share a common center C or have respective centers that are within a fraction of an inch of each other). In some implementations, each enhanced retroreflective marker has a uniform refractive index. The enhanced retroreflective markers in this description include markers that are true retroreflectors as well as markers that substantially retroreflect.

Figure 2A:
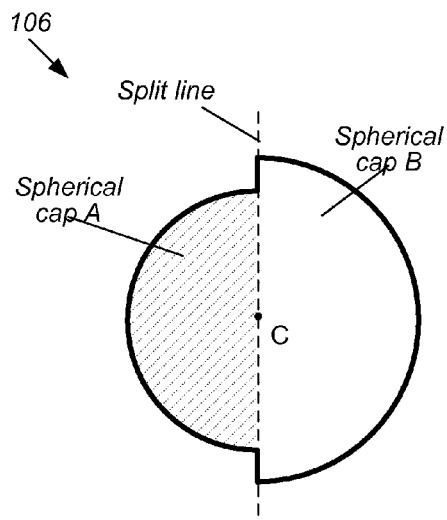
FIGS. 2a, 2b, 2c, and 2d each shows a cross-sectional view of an enhanced retroreflective marker.
Figure 2B:
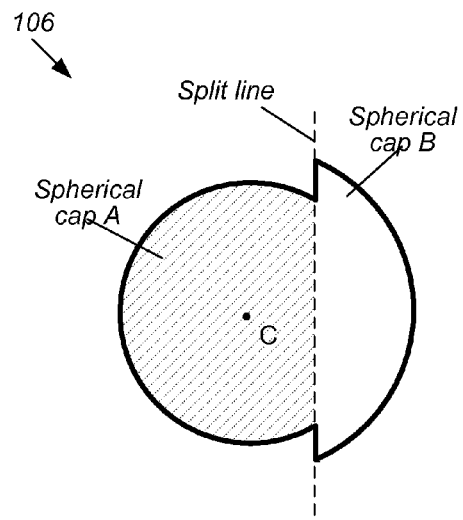
Figure 2C:
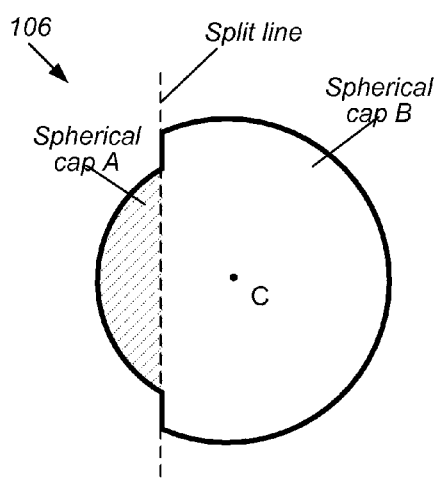
Figure 2D:
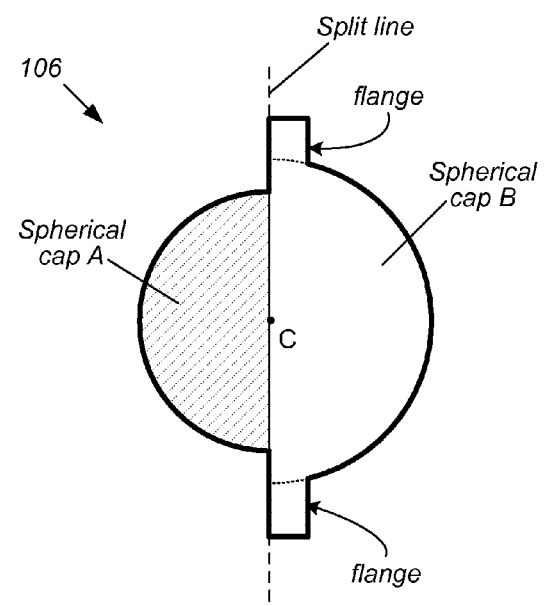

The term "split line" as used in this description refers to a plane that generally divides the enhanced retroreflective marker between the two spherical caps that define its shape. Although the split line of the enhanced retroreflective marker of FIG. 2a passes through the common center C, an enhanced retroreflective marker 106 may be implemented such that the split line is high relative to the common center (as shown in FIG. 2b) or low relative to the common center (as shown in FIG. 2c). In the implementation of FIG. 2d, the shape of the enhanced retroreflective marker is further defined by flanges that may subsequently by used to facilitate the mounting of the marker to the tool or aid in the manufacturing of the marker.

Figure 3A:
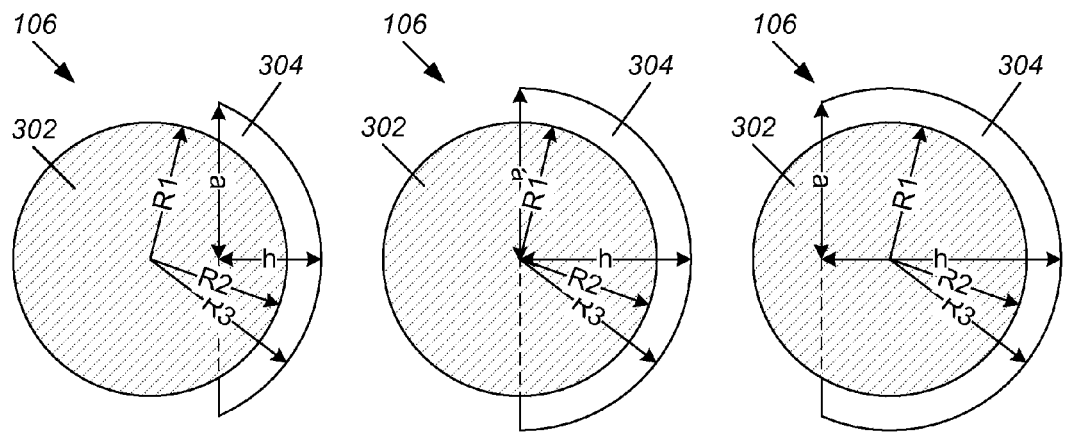
FIGS. 3a and 3b show cross-sectional views of five enhanced retroreflective markers, each formed by a sphere and a spherical cavity.
Figure 3B:
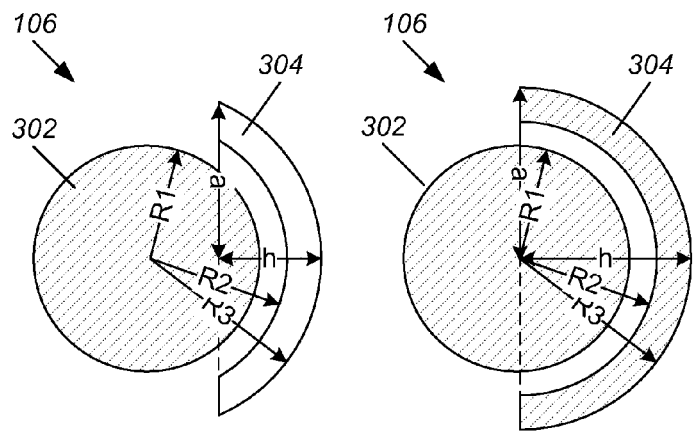

Each implementation of an enhanced retroreflective marker 106 depicted in FIG. 3a is formed by physically coupling (e.g., using an optical coupling adhesive or overmolding and/or potting techniques) a sphere 302 and a spherical cavity 304 at a common boundary between an outer surface of the sphere 302 and an inner surface of the spherical cavity 304. Each implementation of an enhanced retroreflective marker 106 depicted in FIG. 3b is formed by a sphere 302 and a spherical cavity 304 that are separated by a medium (e.g., air). In the implementations depicted in both FIGS. 3a and 3b, the sphere 302 is defined by a radius R1, and the spherical cavity 304 is defined by an inner radius R2, an outer radius R3, a height h, and a base radius a.

Figure 4:
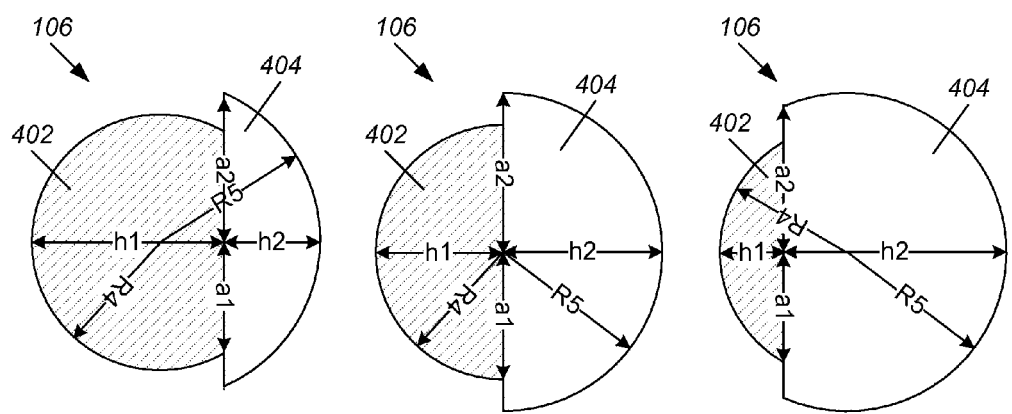
FIG. 4 shows cross-sectional views of three enhanced retroreflective markers, each formed by two spherical caps.

Each implementation of an enhanced retroreflective marker 106 depicted in FIG. 4 is formed by physically coupling (e.g., using an optical coupling adhesive) two spherical caps at a common boundary. One of the spherical caps 402 is defined by a radius R4, a height h1, and a base radius a1, and the other spherical cap 404 is defined by a radius R5, a height h2, and a base radius a2.

Figure 5:
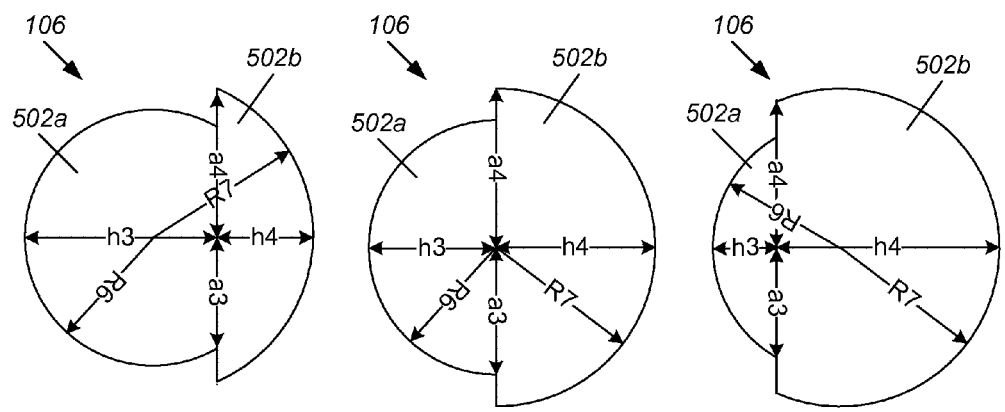
FIG. 5 shows cross-sectional views of three enhanced retroreflective markers, each formed by an integral unit defined by two spherical cap components.

Each implementation of an enhanced retroreflective marker 106 depicted in FIG. 5 is formed as a single integral unit (e.g., using embossing or micro-embossing techniques to deform a substrate between two patterned tools and embossing the shape of the marker into the substrate, injection molding techniques, and techniques that involve machining and/or etching the marker out of a single solid piece of material) having two spherical cap components. One of the spherical cap components 502a is defined by a radius R6, a height h3, and a base radius a3, and the other spherical cap component 502b is defined by a radius R7, a height h4, and a base radius a4.

Other characteristics of an enhanced retroreflective marker may be varied based on the environmental context (e.g., indoors or outdoors) in which a marker-tracking system is to be deployed and/or the application context (e.g., medical or industrial) in which marker-tracking system is to be applied. Examples of such characteristics include:

(1) the material(s) used to form the enhanced retroreflective marker—varying the material(s) affects the refractive index of the enhanced retroreflective marker, the marker's ability to function accurately even when exposed to harsh environmental conditions, and/or the marker's cost if a less expensive material may be used in lieu of a more expensive material. The enhanced retroreflective marker may be formed of a material having a relatively low refractive index ($n \leq 1.9$), such as polycarbonate, or a relatively high refractive index ($n > 1.9$), such as a specialized glass;

(2) the size of the enhanced retroreflective marker—depending on its application, the enhanced retroreflective marker can be built to any size (e.g., a thousandth of an inch in diameter or an inch in diameter) and used alone or as part of a group of enhanced retroreflective markers that are clustered together or positioned such that a space exists between each individual marker;

(3) the location of the split line between the two spherical caps that define a shape of the enhanced retroreflective marker; and (4) the amount of a rear or outside surface of the enhanced retroreflective marker that is reflectorized using any one of a number of techniques known in the art, including but not limited to silvering, painting, direct metallization, and placement of the rear or outside surface of the marker into a reflective medium.

Items (3) and (4) above are discussed in more detail as follows.

Figure 6A:
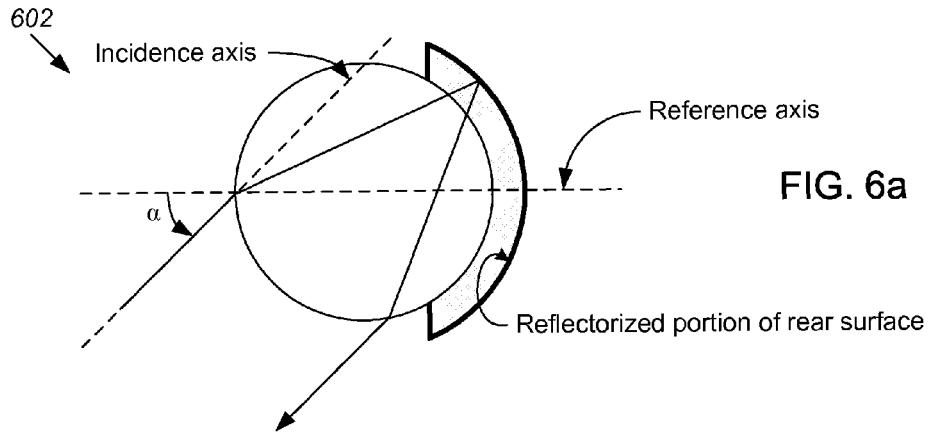
FIG. 6a shows a path of light with respect to an enhanced retroreflective marker having a high split line and a fully-reflectorized rear surface.
Figure 6B:
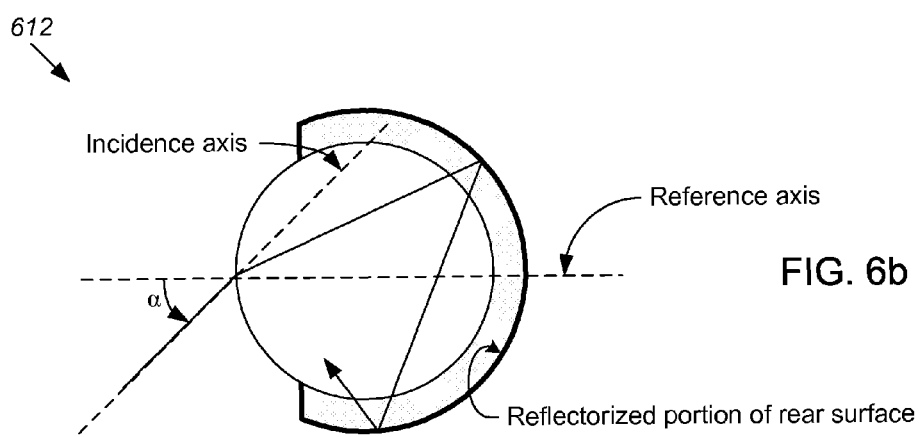
FIG. 6b shows a path of light with respect to an enhanced retroreflective marker having a low split line and a fully-reflectorized rear surface.
Figure 6C:
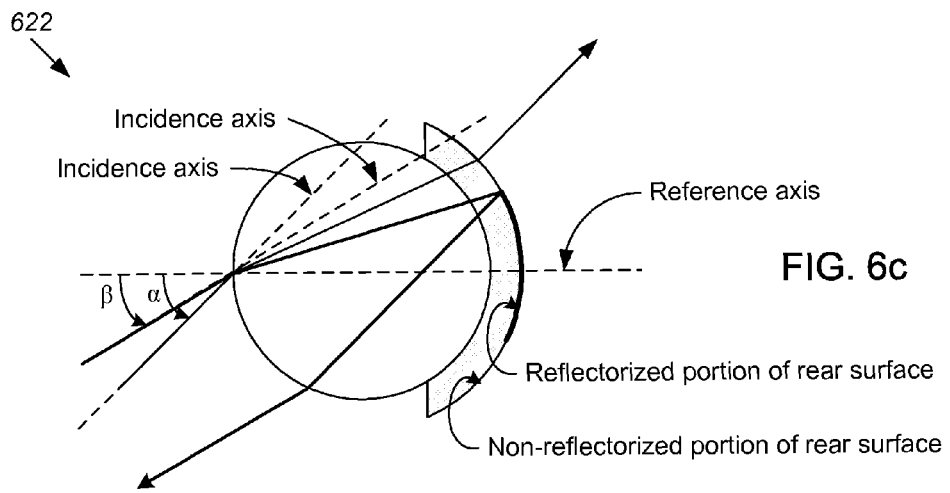
FIG. 6c shows paths of light with respect to an enhanced retroreflective marker having a high split line and a partially-reflectorized rear surface.

FIGS. 6a and 6b show examples of enhanced retroreflective markers 602, 612 having different split lines. Suppose the entirety of the rear surface of each of the markers 602, 612 is reflectorized and light enters each of the markers 602, 612 at an identical high entrance angle $\alpha°$. In the case of the marker 602, the high split line enables an input light ray to pass through the marker 602, reflect off the reflectorized rear surface, and exit the marker 602 as shown in FIG. 6a. By contrast, the low split line of the marker 612 results in the reflected light exiting the marker 612 non-parallel to the input light ray as shown in FIG. 6b. FIGS. 6a and 6c show examples of enhanced retroreflective markers 602, 622 having identical split lines but different amounts of reflectorized rear surfaces. Suppose light enters each of the markers 602, 622 at the high entrance angle $\alpha°$. In the case of the marker 622, the incoming light passes through the marker 622, hits a non-reflectorized portion of the rear surface of the marker 622, and exits the marker 622 as shown in FIG. 6c. The examples of FIGS. 6a, 6b, and 6c illustrate the manner in which an enhanced retroreflective marker may be tuned (by varying the split line location and/or the size of the reflectorized rear surface) so that its retroreflective capability is "turned on" only when light enters the marker within entrance angles (referred to in this description as "effective range of entrance angles") that range between $0°$ and $\pm\beta°$.

Inclusion of enhanced retroreflective markers, each having a limited effective range of entrance angles, in a retroreflective marker-tracking system may improve the system's position tracking accuracy by preventing distal markers (located in a background relative to an observation point) from interfering with proximal markers (located in a foreground relative to the observation point). FIG. 7a shows an example of a device 702 to which five multi-lens high refractive index markers 704 are affixed. Taken together, the five multi-lens high refractive index markers 704 enable the device 702 to be viewed for a full 360° rotation. If a distal marker 704a does not stop retro-reflecting when it is not being tracked, the distal marker 704a can interfere with the proximal marker 704b that is the subject of the tracking when the distal marker 704a moves behind the proximal marker 704b and the two reflective sources merge into one. In such cases, the proximal marker 704b and the distal marker 704a appear to an observation point 706 of the retroreflective marker-tracking system to be a single irregularly-shaped marker 708 (as shown in FIG. 7b), thus resulting in the position of the device 702 being inaccurately determined. FIG. 7c shows a device 712 having five enhanced retroreflective markers 714 affixed thereto. If a distal marker 714a is tuned to stop retroreflecting when light enters the distal marker 714a outside of its effective range of entrance angles, a proximal marker 714b can be viewed by the retroreflective marker-tracking system without distortion (as shown in FIG. 7d), thus resulting in an accurate determination of the position of the device 702.

In addition to avoiding "marker merging" as described in the previous paragraph, the inclusion of enhanced retroreflective markers, each having a limited effective range of entrance angles, may also improve the position tracking accuracy of a marker-tracking system in those instances in which the enhanced retroreflective marker is partially occluded by an obstruction.

Figure 8A:
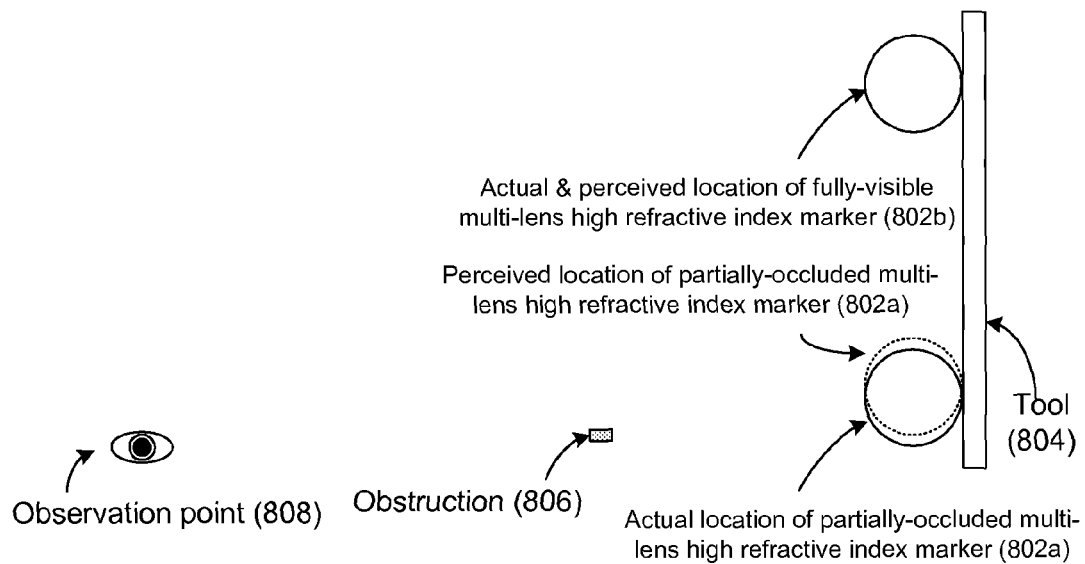
FIG. 8a shows a retroreflective marker-tracking system in which multi-lens high refractive index retroreflective markers are deployed.
Figure 8B:
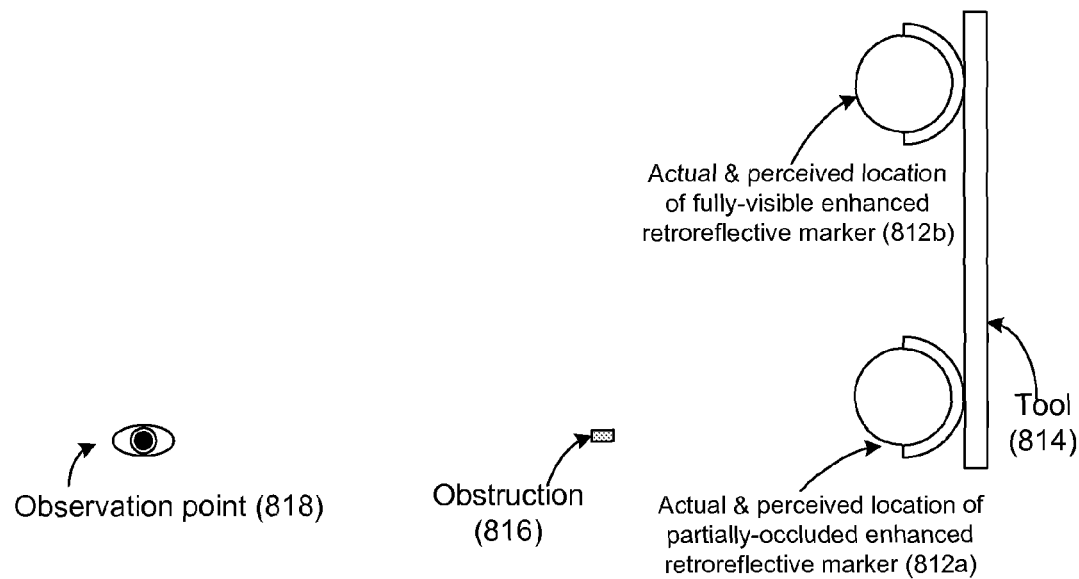
FIG. 8b shows a retroreflective marker-tracking system in which enhanced retroreflective markers are deployed.

FIG. 8a shows an example of a marker-tracking system in which two multi-lens high refractive index markers 802a, 802b are deployed; FIG. 8b shows an example of a marker-tracking system in which two enhanced retroreflective markers 812a, 812b of the type depicted in FIGS. 2, 3, 4, and 5 are deployed. Suppose, for example, that each of the marker-tracking systems of FIG. 8a and FIG. 8b are implemented to determine a position of a marker using an algorithm that is based on a calculated center of mass of the marker using the centroid of the reflected light image.

In the case of FIG. 8a, the multi-lens high refractive index marker 802a is partially occluded by an obstruction 806 and the center of mass of the partially-occluded marker 802a (as viewed by an observation point 808 of the marker-tracking system of FIG. 8a) appears to shift towards the fully-visible marker 802b. This has the effect of introducing inaccuracies in determining the position of a tool 804 (to which the multi-lens high refractive index markers 802 are affixed) as the perceived location of the partially-occluded marker 802a and the actual location of the partially-occluded marker 802a are out of sync.

Figure 8C:
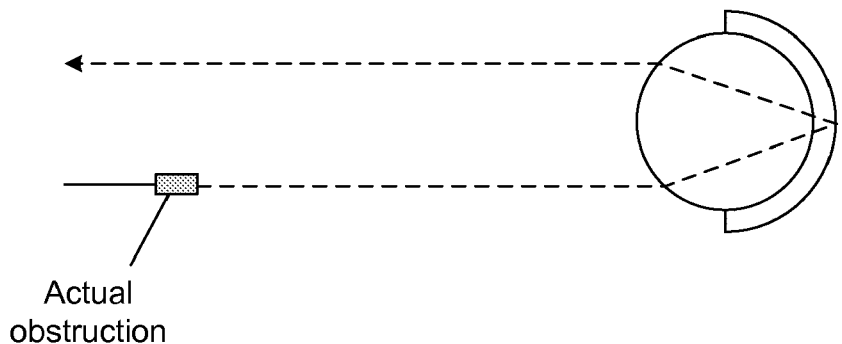
FIG. 8c shows a side view of a light path with respect to a partially-occluded enhanced retroreflective marker of FIG. 8b.
Figure 8D:
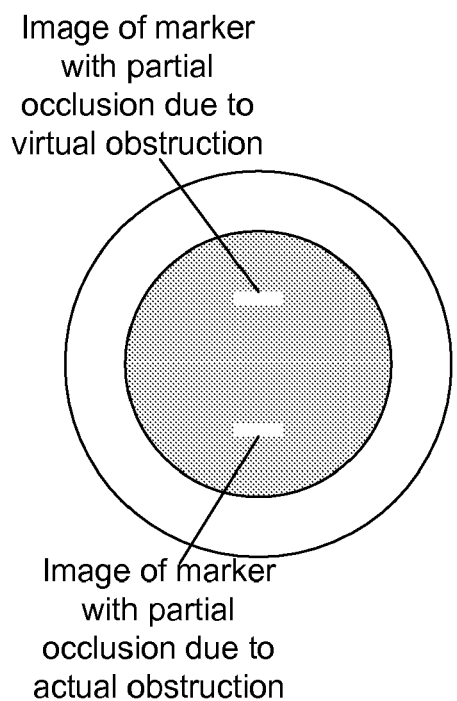
FIG. 8d shows a front view of the partially-occluded enhanced retroreflective marker of FIG. 8b.
Figure 9:
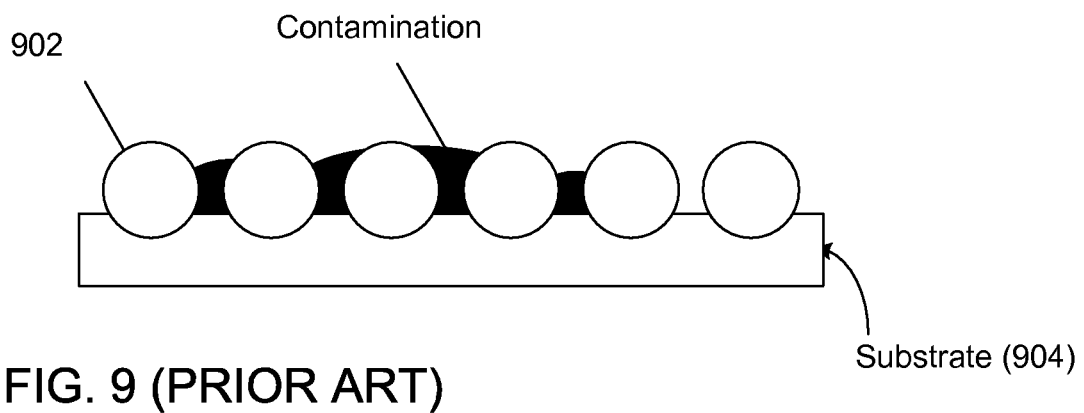
FIG. 9 shows tiny glass beads embedded in a substrate.

By contrast, an enhanced retroreflective marker 812a that is partially-occluded by an obstruction 816 will appear to an observation point 818 of the marker-tracking system of FIG. 8b to be partially-occluded by two obstructions: an actual obstruction and a virtual obstruction, as shown in FIGS. 8c and 8d. Since any occlusion that happens in one area of the enhanced retroreflective marker 812a has a reflected counterpart on the opposite side of the enhanced retroreflective marker 812a, the image observed by an observation point 818 of the marker-tracking system of FIG. 8b appears to be symmetrical about the reference axis, and the center of mass of the enhanced retroreflective marker 812a remains unchanged. Accordingly, the position of the tool 814 may be accurately determined as the perceived location of the partially-occluded enhanced retroreflective marker 812a and the actual location of the partially-occluded enhanced retroreflective marker 812a are in sync.

In some implementations, the outside surface (front and/or rear) of an enhanced retroreflective marker is configured to diffusely reflect light to provide a less intense but more consistent retroreflective target for a marker-tracking system. In some implementations, an enhanced retroreflective marker is manufactured using a translucent material such that the marker diffusely retroreflects light. In this manner, the position of the enhanced retroreflective marker may be more accurately determined by the marker-tracking system.

Generally, an enhanced retroreflective marker is configured such that light rays exiting the marker are substantially parallel to the input rays. In those instances in which the marker illuminating device is at a different location than the observation point, a slight convergence and/or divergence in the returned light rays may be desirable. Retroreflection falls off rapidly when the angle (the "observation angle") between the marker illuminating device and the observation point increases. In such instances, an enhanced retroreflective marker can be tuned to optimize the inverse square relationship with distance of the illumination so that the intensity of the reflected light image remains relatively constant even as the observation angle varies. This tuning may involve altering the ratio of the radii of the spherical caps that define the shape of the enhanced retroreflective marker, altering the material(s) used to form the enhanced retroreflective marker, or both.

Although the examples described above refer to a marker-tracking system that is deployed in a medical application context, the enhanced retroreflective marker may also be included in a marker-tracking system that is deployed in an industrial application context for use in a wide array of computer-aided measurement solutions (e.g., dynamic motion measurement, co-ordinate measurement, and scanner tracking). Accordingly, the object to which an enhanced retroreflective marker is affixed to may be any animate or inanimate object.

Particular implementations of the subject matter described in this specification have been described. Other implementations are within the scope of the following claims.

What is claimed is:

1. A system comprising:
an object to be tracked including a first retroreflective marker having a substantially spherical shape comprising a first spherical cap having a first diameter and a second spherical cap having a second diameter greater than the first diameter, the first spherical cap and the second spherical cap being disposed substantially concentric in relation to one another, a split line defining a plane that intersects the caps, wherein the second spherical cap terminates at the split line,
a portion of a surface of an outer edge of at least one of the first and second spherical caps having a reflective material, thereby providing retroreflection from the marker;
a marker illuminating device configured to illuminate the first retroreflective marker;
a marker sensing device configured to detect the illuminated first retroreflective marker and for generating first data indicative of the location of the illuminated first retroreflective marker in space; and
a computing device configured to process the first data generated by the marker sensing device to determine a position of the object in space.

2. The system of claim 1, wherein the shape of the first retroreflective marker is further defined by one or more flanges.

3. The system of claim 1, wherein the first retroreflective marker has a uniform refractive index.

4. The system of claim 1, wherein the first spherical cap comprises a sphere and the second spherical cap comprises a spherical cavity, the first spherical cap and the second spherical cap separated by a medium.

5. The system of claim 4, wherein:
the sphere is defined by a radius R1; and
the spherical cavity is defined by an inner radius R2, an outer radius R3, a height h, and a base radius a.

6. The system of claim 4, wherein the outer radius R3 of the spherical cavity is equal to the height h of the spherical cavity.

7. The system of claim 4, wherein the outer radius R3 of the spherical cavity is greater than the height h of the spherical cavity.

8. The system of claim 4, wherein the outer radius R3 of the spherical cavity is less than the height h of the spherical cavity.

9. The system of claim 4, wherein the inner radius R2 of the spherical cavity is equal to the radius R1 of the sphere.

10. The system of claim 4, wherein the inner radius R2 of the spherical cavity is greater than the radius R1 of the sphere.

11. The system of claim 10, wherein the reflective material is applied directly on a medium-side surface of the spherical cavity.

12. The system of claim 10, wherein the reflective material is applied directly on a non-medium-side surface of the spherical cavity.

13. The system of claim 4, wherein the reflective material is applied directly on a surface of the sphere.

14. The system of claim 4, wherein the reflective material is applied directly on a non-medium-side surface of the spherical cavity.

15. The system of claim 1, wherein:
the first spherical cap is further defined by a radius R4, a height h1, and a base radius a1; and
the second spherical cap is further defined by a radius R5, a height h2, and a base radius a2.

16. The system of claim 15, wherein the height h1 is greater than the radius R4.

17. The system of claim 15, wherein the height h2 is greater than the radius R5.

18. The system of claim 15, wherein the height h1 is substantially equal to the radius R4 and the height h2 is equal to the radius R5.

19. The system of claim 1, wherein the reflective material is applied directly on a surface of the first spherical cap.

20. The system of claim 1, wherein the reflective material is applied directly on a surface of the second spherical cap.

21. The system of claim 1, wherein the first spherical cap and the second spherical cap are constructed as an integral unit.

22. The system of claim 21, wherein:
the first spherical cap is further defined by a radius R6, a height h3, and a base radius a3; and
the second spherical cap is further defined by a radius R7, a height h4, and a base radius a4.

23. The system of claim 22, wherein the height h3 is greater than the radius R6.

24. The system of claim 22, wherein the height h4 is greater than the radius R7.

25. The system of claim 22, wherein the height h3 is equal to the radius R6 and the height h4 is substantially equal to the radius R7.

26. The system of claim 21, wherein the reflective material is applied directly on a surface of the first spherical cap.

27. The system of claim 21, wherein the reflective material is applied directly on a surface of the second spherical cap.

28. The system of claim 1, wherein the first retroreflective marker is formed of a shatter-resistant material.

29. The system of claim 1, wherein the first retroreflective marker is formed of a material having a relatively low refractive index.

30. The system of claim 1, wherein the first retroreflective marker is formed of a material having a relatively high refractive index.

31. The system of claim 1, wherein the reflective material is applied directly on a rear surface of the first retroreflective marker.

32. The system of claim 1, wherein the reflective material is applied directly on one or more portions of a rear surface of the first retroreflective marker.

33. The system of claim 32, wherein the one or more portions of the rear surface of the retroreflective marker upon which the reflective material is applied comprises less than an entirety of the rear surface.

34. The system of claim 1, wherein the first retroreflective marker is configured to diffusely retroreflect light.

35. The system of claim 1, wherein the object further includes at least one other retroreflective marker having a substantially spherical shape comprising a first spherical cap having a first diameter and a second spherical cap having a second diameter greater than the first diameter, the first spherical cap and the second spherical cap being disposed substantially concentric in relation to one another, a split line defining a plane that intersects the caps, wherein the second spherical cap terminates at the split line,
a portion of a surface of an outer edge of at least one of the first and second spherical caps having a reflective material, thereby providing retroreflection from the marker.

36. The system of claim 35, wherein the first retroreflective marker and the at least one other retroreflective marker are disposed on the object relative to one another such that only one of the retroreflective markers retroreflects light at a time when the retroreflective markers are simultaneously illuminated by the marker illuminating device.

37. The system of claim 35, wherein the first retroreflective marker and the at least one other retroreflective marker are disposed on the object relative to one another such that at least two retroreflective markers retroreflect light when the retroreflective markers are simultaneously illuminated by the marker illuminating device.

38. The system of claim 37, wherein the marker sensing device is further configured to detect the at least one other illuminated retroreflective marker and generate data indicative of the location of each of the illuminated markers in space.

39. The system of claim 38, wherein the computing device processes the data generated by the marker sensing device to determine the position and/or orientation of the object in space.

40. The system of claim 35, wherein the retroreflective markers are sized and dimensioned such that the marker sensing device detects a single discrete source of reflected light when the marker illuminating device illuminates the retroreflective markers simultaneously.

41. The system of claim 35, wherein the retroreflective markers are sized and dimensioned such that the marker sensing device detects multiple discrete sources of reflected light when the marker illuminating device illuminates the retroreflective markers simultaneously.

42. The system of claim 41, wherein at least one of the multiple discrete sources of reflected light is formed when the marker illuminating device illuminates at least two retroreflective markers simultaneously.

43. The system of claim 1, wherein the diameters of the first and second spherical caps are selected so that an intensity of a reflected light image that is detected when the first retroreflective marker is illuminated remains relatively constant even as an observation angle between the marker illuminating device and the marker sensing device varies.

* * * * *

UNITED STATES PATENT AND TRADEMARK OFFICE
CERTIFICATE OF CORRECTION

| | | |
|---|---|---|
| PATENT NO. | : 7,945,311 B2 | Page 1 of 1 |
| APPLICATION NO. | : 11/673131 | |
| DATED | : May 17, 2011 | |
| INVENTOR(S) | : Bradley J. McCloy and Georg Brunner | |

It is certified that error appears in the above-identified patent and that said Letters Patent is hereby corrected as shown below:

Column 9, Line 14-15, in Claim 18, after "is" delete "substantially"

Column 9, Line 34, in Claim 25, after "is" delete "substantially"

Signed and Sealed this
Fifth Day of July, 2011

David J. Kappos
*Director of the United States Patent and Trademark Office*